(12) United States Patent
Ballato

(10) Patent No.: US 8,020,432 B1
(45) Date of Patent: Sep. 20, 2011

(54) ACOUSTIC MICROELECTROMECHANICAL VISCOMETER

(75) Inventor: Arthur Ballato, Oceanport, NJ (US)

(73) Assignee: The United States of America as represented by the Secretary of the Army, Washington, DC (US)

(*) Notice: Subject to any disclaimer, the term of this patent is extended or adjusted under 35 U.S.C. 154(b) by 402 days.

(21) Appl. No.: 12/453,489

(22) Filed: Apr. 29, 2009

(51) Int. Cl.
*G01N 11/10* (2006.01)

(52) U.S. Cl. ..................... 73/54.41; 73/54.39

(58) Field of Classification Search ............. 73/54.41, 73/54.39
See application file for complete search history.

(56) References Cited

U.S. PATENT DOCUMENTS 7,518,949 B2 * 4/2009 Haugland ............... 367/31

* cited by examiner

*Primary Examiner* — Hezron E Williams
*Assistant Examiner* — Rodney T Frank
(74) *Attorney, Agent, or Firm* — Michael Zelenka; Stephen J. Harbulak

(57) ABSTRACT

A rigid, planar, non-resonating boundary is introduced parallel to the surface of the piezoelectric resonator in a measurand chamber in order to both reduce the separation space (l) between the resonator and confining wall and confine the measurand fluid between those surfaces in order to reliably measure acoustic viscosity independently form the mass density ($\rho$) of the measurand fluid. The hypothesis is that when the penetration depth ($\delta$) is comparable to the separation distance (l) between the resonator and the confining wall, then resonator perturbation is a sensitive function of the abbreviated separation space. Variations in the spacing between the resonator and confining wall are accomplished by adjusting the rigid, planar, non-resonating boundary, or confining wall, with a means for lateral movement. The ability to accurately adjust and control small spaces thereby enables MEMS versions of viscometers and associated types of fluid sensors.

20 Claims, 5 Drawing Sheets

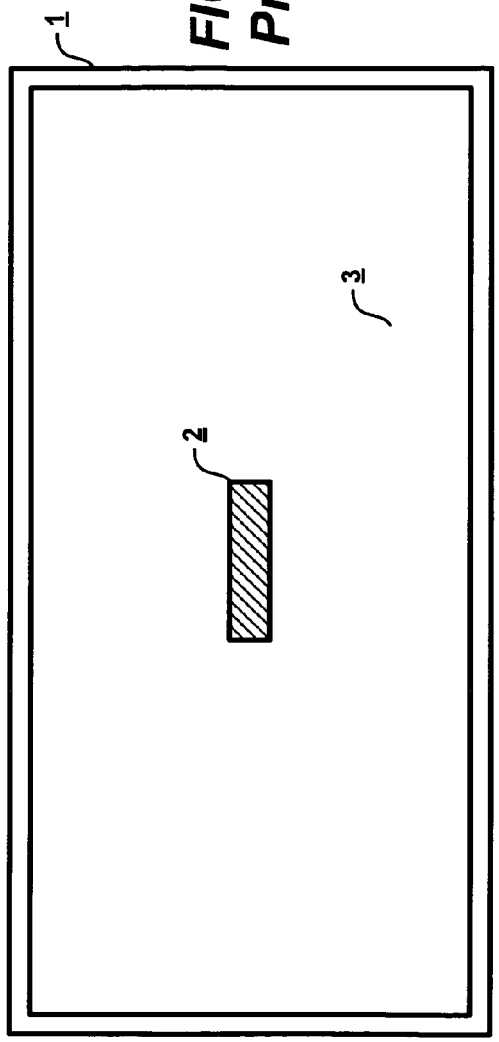
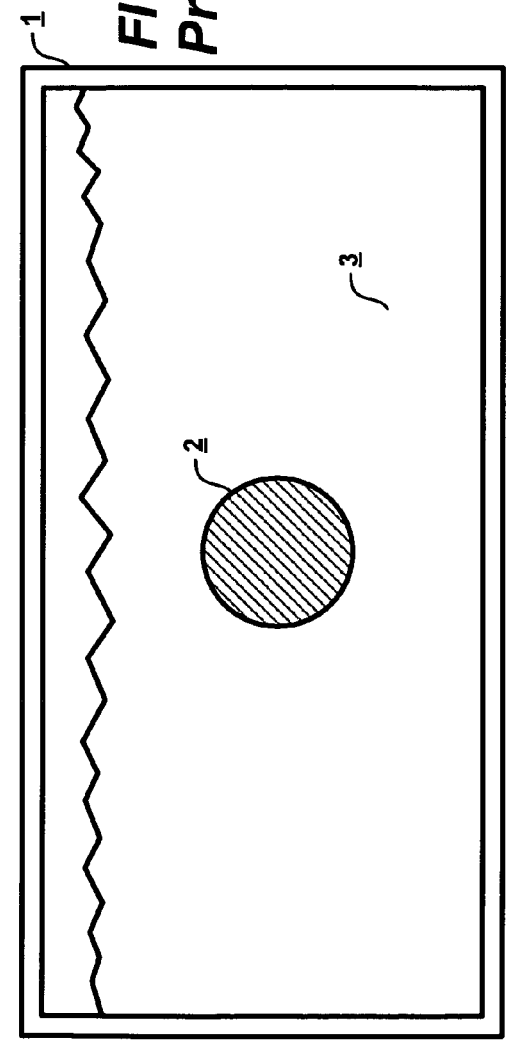

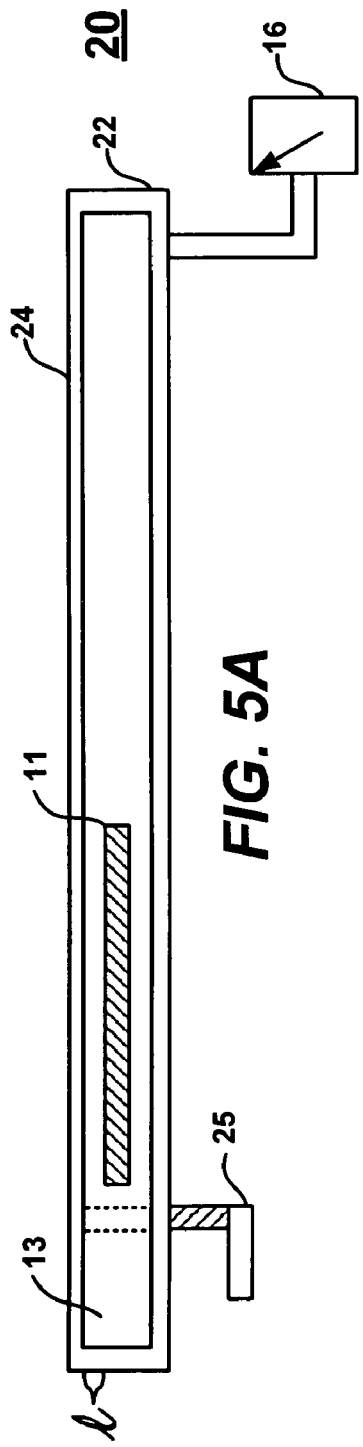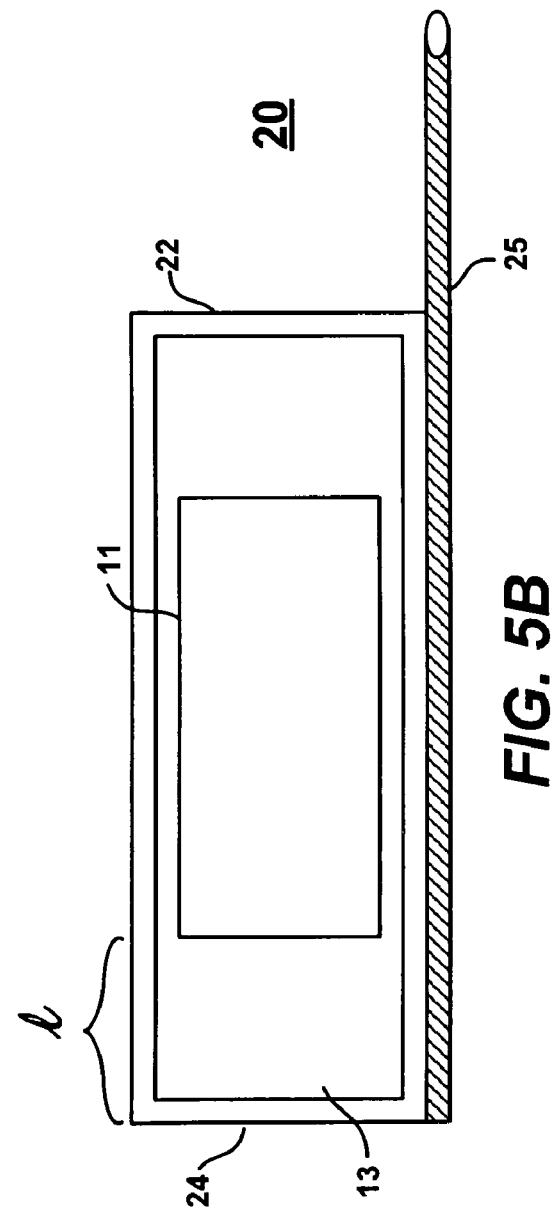
FIG. 5A
FIG. 5B

ACOUSTIC MICROELECTROMECHANICAL VISCOMETER

GOVERNMENT INTEREST

The invention described herein may be manufactured, used, imported, sold, and licensed by or for the Government of the United States of America without the payment to me of any royalty thereon.

FIELD OF THE INVENTION

This invention relates in general to field of solid-state acoustic devices. In particular, this invention relates to an acoustic micro-electromechanical viscometer.

BACKGROUND OF THE INVENTION

Several approaches for measuring fluid shear viscosities using quartz crystals have evolved since Quimby originated the technique of measuring solids by attaching them to a quartz crystal. The Quimby composite resonator (QCR) functions like a quartz crystal microbalance (QCM) in the limit where the measurand becomes a thin film, and its elasticity is neglected. Mason first adapted the technique for measuring liquids, and this method is still widely used. Stockbridge has also used quartz crystal techniques to measure gases. In these applications, the crystal resonator is measured without, and then with, the loading of the measurand fluid. Ensuing changes can be recorded as changes in frequency, phase, or impedance level, from which the unknown measurand properties can then be inferred.

Prior art devices have provided numerous equivalent electrical circuits that model the piezoresonator, and describe the behavior of the piezoresonator when its surface is subjected to various loading conditions. The most popular equivalent electrical circuit is the Butterworth-Van Dyke (BVD) network, which consists of a capacitance $C_0$, shunted by an $R_1$, $L_1$, and $C_1$ series arm. The series arm is the manifestation of the piezoelectrically induced vibratory motion at a single isolated resonance. The BVD lumped circuit then evolved into the more elaborate broad-band, multi-mode, transmission-line networks that place the mechanical boundary loadings and piezoelectric excitation mechanism in series at the surfaces. Current dynamic techniques for measuring fluid shear viscosities using quartz, or other piezoelectrics, rely upon exposing the resonator surface to a measurand tank whose extent greatly exceeds the penetration depth ($\delta$) of the evanescent shear mode excited by the active element. This configuration allows the effect of the loading parameters to be expressed concisely. Perturbation of the electrical equivalent circuit parameters of the resonator by the fluid loading permits calculation of the mass density—shear viscosity product, but does not allow calculation of these quantities separately.

FIGS. 1A and 1B are top and end views of a typical prior art measurand tank.

Referring now to FIG. 1A, the prior art measurand tank 1 contains a shear wave piezoelectric transducer 2 that is submerged in the measurand fluid 3. The piezoelectric transducer 2 produces acoustic motion in the fluid 3 and also senses the effect of that motion on the fluid 3. The waves at the top of fluid 3 represent the fluid being a liquid, however whenever the fluid is a gas, those skilled in the art will appreciate that measurand tank 1 can be equipped with a suitable lid and input and output valves. In all cases, one or both surfaces of the piezoelectric resonator need to be in contact with the measurand fluid. Lord Rayleigh, commenting on Stokes' treatment of fluid viscosity, wrote in §347 of his Theory of Sound, Vol. 2, 2nd revised edition, (1896): "The velocity of the fluid in contact with the plane is usually assumed to be the same as that of the plane itself on the apparently sufficient ground that the contrary would imply an infinitely greater smoothness of the fluid with respect to the solid than with respect to itself." This assumption is implicit throughout this document; it means simply that the fluid immediately adjacent to a moving resonator surface has the same velocity as that surface, and the fluid immediately adjacent to a motionless solid wall has zero velocity. An unbounded Newtonian fluid, i.e., a fluid with shear viscosity, in addition to the usual attributes of mass density, $\rho$, and elastic stiffnesses, $c_S$ and $c_L$, that is in intimate contact with a resonator surface of area A, presents to the surface both shear (S) and longitudinal (L) impedances. These depend on angular frequency, $\omega=2\pi f$, where f is the frequency in hertz.

Mechanical shear impedance is $Z_S=A\sqrt{(j\omega\eta\rho)}=R_S+j\omega L_S$, where mechanical resistance $R_S$ represents shear dissipation and mechanical inductance $L_S$ models entrained mass loading. Penetration depth is $\delta=\lambda/2\pi=\sqrt{(2\eta/\rho\omega)}$, where $\lambda$ is the acoustic wavelength. Longitudinal impedance is given by the formula $R_L$ (mechanical ohms)$=A\rho v_L=A\sqrt{(\rho c_L)}$, where $v_L$ is the longitudinal of acoustic waves in the fluid. This mechanical resistance represents energy radiating into the measurand fluid; we neglect longitudinal viscosity. These impedances, transformed by a piezoelectric factor, appear in the BVD circuit in series with the $R_1$, $L_1$, and C1 branch. Thus, immittance (a word meaning either impedance or admittance) and/or frequency measurements on a resonator immersed in an unbounded fluid, i.e. when the separation distance (l) from the resonator surface to a confining surface greatly exceeds the penetration depth ($\delta$), yield only the longitudinal elastic stiffness ($\rho c_L$) and Newtonian viscosity ($\eta\rho$) products.

Although prior art dynamic techniques for measuring fluid shear viscosities using quartz, or other piezoelectrics and the equivalent circuits have proven to be quite beneficial, they are still subject to a number of limitations based on the resonator surface being exposed to a measurand tank where the separation distance (l) between the resonator surface and the confining surfaces of the measurand tank greatly exceeds the penetration depth ($\delta$) of the evanescent shear mode excited by the active element. There is currently no reliable way to measure the quantities $\eta$ (viscosity) and $\rho$ (mass density) separately. The shortcomings, disadvantages, and limitations of measuring the viscosity-density product in such prior art measurements include, inter alia, the requirement for additional measurements of density. These additional measurements are not a part of an integrated measurement protocol, and are made by other instruments in other setups, leading to inaccuracies due to non-simultaneity of measurements, variations in temperature, and other factors well known to those practiced in the art.

Thus, there has been a long-felt need for a means of obtaining both acoustic shear viscosity and density as separate quantities, simultaneously, and with the same apparatus. The present invention overcomes and obviates the shortcomings, limitations, and disadvantages of prior art measuring systems.

SUMMARY OF THE INVENTION

In an effort to satisfy the long-felt need for measuring acoustic viscosity directly for many fluids and ambient conditions of interest, this invention discloses the novel and utile advantages employing the unexplored regime where penetration depth ($\delta$) of the fluid occupying the intervening region between the resonator and a confining wall is comparable in size to the separation distance (l) between the resonator and the confining wall. This regime is much more complicated than the traditional one of the resonator being exposed to a bath of fluid whose extent greatly exceeds the penetration depth (δ). It is also more complicated both in the theoretical analysis, and in the experimental realization of the conditions for operation. To explore these complexities and advantages, this invention introduces a planar rigid boundary that is positioned parallel to the surface of the piezoelectric resonator in the measurand chamber in order to both reduce the separation space (l) between the resonator and confining wall and confine the measurand fluid between those surfaces in a new and innovative measuring arrangement. After making the separation distance (l) comparable to the penetration depth (δ) in this way it was found that the above-quoted impedance formulas no longer applied due to separation distance (l). Thus, we have hypothesized that when the penetration depth (δ) is comparable to the separation distance (l) between the resonator and the confining wall that resonator perturbation is a sensitive function of the abbreviated separation space.

This important fact permits drastic miniaturization as an extremely advantageous concomitance, since for gases between 200° K and 400° K, pressures between 0.01 to 100 atm, and frequencies (f) between 10 MHz and 1 GHz, the penetration depth (δ) can vary from micrometers to nanometers. Variations in the spacing are effected by using a second, non-resonating piezoelectric, or a device such as an "inchworm" apparatus for the boundary, or confining wall. Such means for accurately adjusting and controlling small spaces are well known in the art. Micro-electro-mechanical (MEMS) versions of viscometers and associated types of fluid sensors are thereby enabled.

Based upon this relationship between a shortened separation distance (l) and resonator perturbation, the present invention provides an acoustic micro-electromechanical viscometer comprising a measurand chamber containing a piezoelectric resonator, where the penetration depth (δ) in the fluid is comparable to the separation distance (l) between the resonator and a rigid, planar, non-resonating boundary, or confining wall. The rigid, planar, non-resonating boundary also advantageously allows for adjustment of the separation space (l).

Accordingly, it is an object of the present invention to provide an acoustic viscometer within a measurand chamber containing a piezoelectric resonator one of whose surfaces is separated from a planar, non-resonant boundary by a separation distance (l) comparable to the penetration depth (δ) of the fluid.

It is another object of the present invention to provide an acoustic micro-electromechanical viscometer within a measurand chamber containing a piezoelectric resonator one of whose surfaces is separated from a planar, non-resonant boundary by a separation distance (l) comparable to the penetration depth (δ) of the fluid.

It is still a further object of the present invention to provide an acoustic micro-electromechanical viscometer with a narrow and shallow measurand chamber containing a piezoelectric resonator one of whose surfaces is separated from a planar, non-resonant boundary by a separation distance (l) comparable to the penetration depth (δ) of the fluid.

It is yet another object of the present invention is to provide methods for measuring acoustic viscosity with an acoustic micro-electromechanical viscometer containing a piezoelectric resonator one of whose surfaces is separated from a planar, non-resonant boundary by a separation distance (l) comparable to the penetration depth (δ) of the fluid.

These and other objects and advantages are provided by the present invention's acoustic micro-electromechanical viscometer. This invention's acoustic micro-electromechanical viscometer comprises a shear wave piezoelectric transducer, a measurand chamber, and a rigid, planar, non-resonating piezoelectric boundary with the measurand chamber. The separation distance (l) between one surface of the resonator and the planar, non-resonant rigid boundary being is to the penetration depth (δ) of the fluid. In accordance with the present invention, it is now possible to measure the acoustic viscosity properties of a measurand fluid without suffering from the disadvantages, shortcomings, and limitations of prior art measuring arrangements that were unable to reliably measure acoustic viscosity alone, but only in combination with the mass density (ρ)

To appreciate the advantages of the present invention, it is necessary better to understand some of the salient characteristics of piezoelectric crystal resonators and confined fluid loading. By reducing the fluid bath to a thin layer that separates the shear-mode resonator from a rigid wall in the fluid bath, the confinement in this way affects the evanescent shear wave in the fluid. Thus, formulas relating fluid properties to the equivalent mechanical circuit values will now depend on the layer thickness (l) being normalized to the penetration depth (δ), or separation distance (l). For the great majority of fluids and ambient conditions and frequencies of interest, the penetration depth (δ) characterizing the evanescent shear wave of the measurand fluid, ranges from micrometers to nanometers at the usual frequencies ordinarily employed. One needs to consider the effect of introducing a planar rigid boundary parallel to the surface of the piezoelectric resonator in order to confine the fluid therebetween. When the separation distance (l) that separates the resonator and boundary surfaces becomes comparable to the penetration depth (δ), then the surface of the resonator sees a complex mechanical admittance of:

$$A \cdot Y_S = A \cdot (G_S + jB_S) = \sqrt{(j/2) \cdot (\delta/\eta)} = \tan[\sqrt{(2/j)} \cdot (l/\delta)]. \quad (1)$$

The complex mechanical impedance is $$Z_S = R_S + jX_S = 1/Y_S. \quad (2)$$

where the symbol "j" represents the square root of negative unity; that is, the "imaginary operator."

With the abbreviations $w=(l/\delta)$ and $p=(\delta/\eta)$, shear conductance, $G_S(w)$, and reactance, $X_S(w)$, are:

$$G_S = g(w) \cdot (p/A) = g(w)/[A\sqrt{(\omega\rho\eta/2)}], \text{ and} \quad (3)$$

$$X_S = x(w) \cdot (A/p) = x(w) \cdot A \sqrt{(\omega\rho\eta/2)}. \quad (4)$$

where g(w) and x(w) are dimensionless factors with the general form of a tan h function with superposed cyclic modulation, and the symbol p is equal to the quotient (δ/η). Referring now to the drawings, FIG. 2 is a chart illustrating the mechanical conductance function g(w) and FIG. 3 is a chart illustrating the mechanical reactance function x(w). The first three extrema of g(w) are 0.68111 at w=0.9375, 0.49093 at w=2.347 and 0.050039 at w=3.929; g(0)=0, and g(∞)=½. The first extremum of x(w) is 1.0178 at w=2.366; x(0)=0, and x(∞)=1. At w=0, the slopes are: dg(0)/dw=+1, and dx(0)/dw=+⅔. Similarly defined factors, b(w), |y(w)|, r(w), |z(w)| behave as follows for w<<1: r(w) and |z(w)| are hyperbolic; |y(w)| is linear, and b(w) is zero, with zero slope.

Now, concerning viscosity and mass density when w<<1, and g(w)≈[dg(w)/dw]·w≈w=(1/δ), then viscosity η may be determined directly from the relation $$A \cdot \eta = (\Delta G_S / \Delta l)^{-1} \qquad (5)$$

Similarly, $$A \cdot \rho = (3/\omega) \cdot ((\Delta X_S / \Delta t)) \qquad (6)$$

Equations (5) and (6) express mechanical values. In order to convert these mechanical values to electrical form, $G_S$ is multiplied, and $X_S$ is divided, by the factor $n^2 = (Ae/t)^2$, where e is an effective piezoelectric stress coefficient, and t is the thickness of the resonator. Thus, for w in the range where g(w) and x(w) are linear, automatic network analyzer, or similar electrical instrument measurements yield direct determinations of viscosity and mass density as separate entities. Heretofore, only the product of viscosity and density was obtainable in a single measurement protocol. As a check, the region w>>1 provides the (ρη) product. Similar results pertain to the use of longitudinal resonators to yield values of the compressional stiffness ($c_L$) directly. Because δ is usually very small, MEMS miniaturization is a natural consequence of using the w<<1 regime.

BRIEF DESCRIPTION OF THE DRAWINGS

FIG. 1A is a top view of a prior art measurand tank;
FIG. 1B is an end view of a prior art measurand tank;
FIG. 5A is a conceptual top view of another embodiment of an acoustic micro-electromechanical viscometer in accordance with the present invention;
FIG. 5B is an conceptual end view of the FIG. 5A embodiment of the acoustic micro-electromechanical viscometer in accordance with the present invention;
Table I is a chart listing the acoustic parameters of water/glycerol mixtures;
Table II is a chart listing the acoustic parameters of various fluids;
Table III is a chart listing the acoustic parameters of argon;
Table IV is a chart listing values of the acoustic parameters of hydrogen; and
Table V is a chart listing the acoustic parameters of oxygen.

DETAILED DESCRIPTION OF THE DRAWINGS

In order to describe the effect of having a rigid wall in close proximity to the surface of a shear wave piezoelectric resonator, with the intervening space occupied by the fluid to be measured, a mechanical analog circuit is employed. This device is well known in the art of modeling such systems. Specifically, the fluid is represented by a short length of transmission line whose characteristic wave number and characteristic impedance have complex values, thus describing the evanescent nature of the shear wave motion in the fluid. The end of the transmission line that represents the surface of the rigid wall is described by an open-circuit. At the other end, the transmission-line immittance is attached to the piezoelectric resonator surface. This immittance gives rise to the $G_S$ and $X_S$ values described above by the application of simple circuit-theory rules well known in the art and literature.

Figure 2:
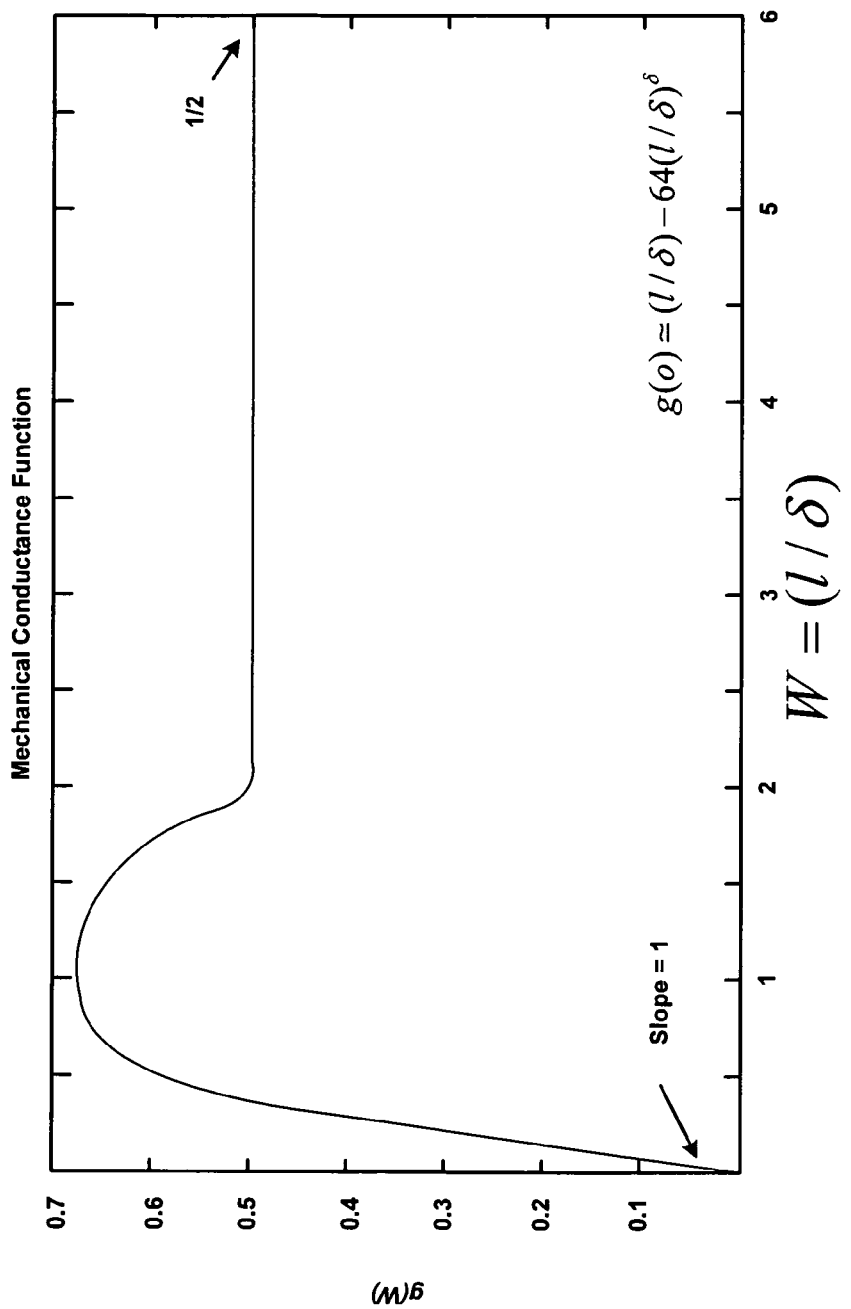
FIG. 2 is a chart illustrating the mechanical conductance function g(w)
Figure 3:
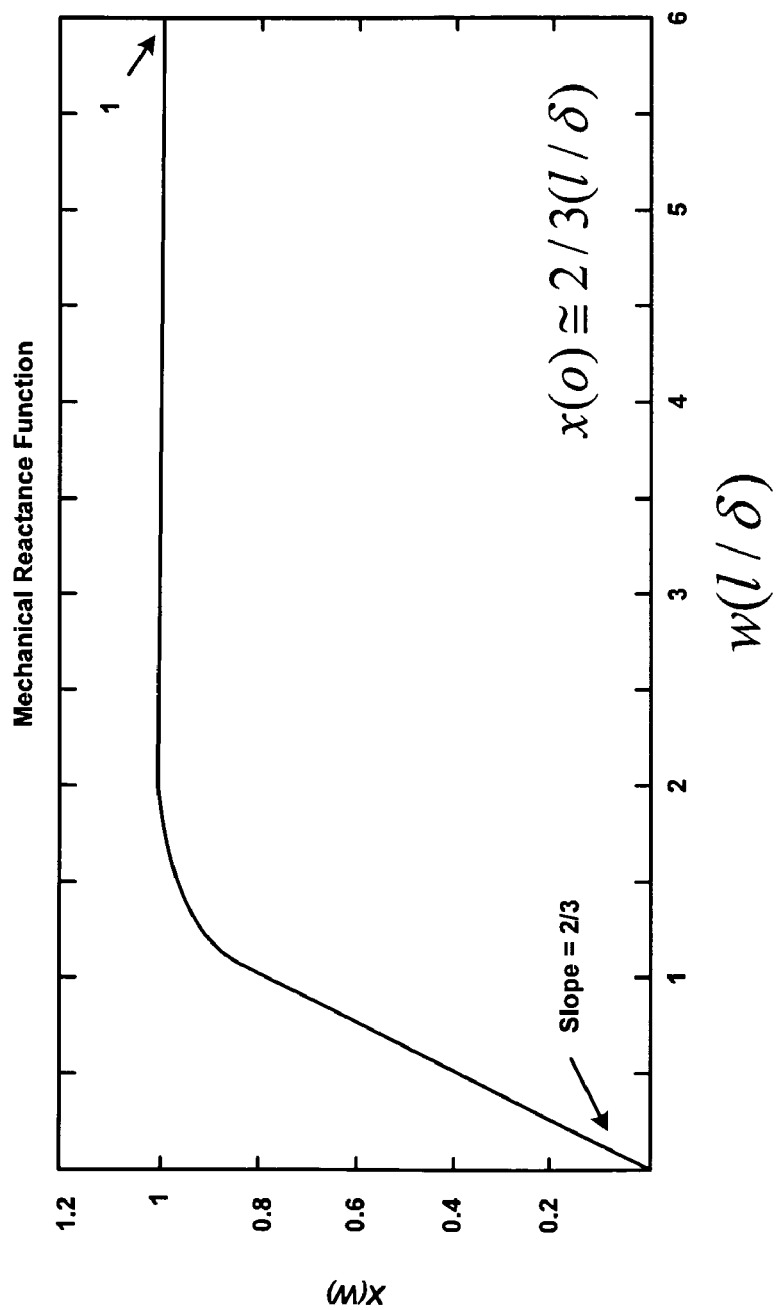
FIG. 3 is a chart illustrating the mechanical reactance function x(w)
Figure 4:
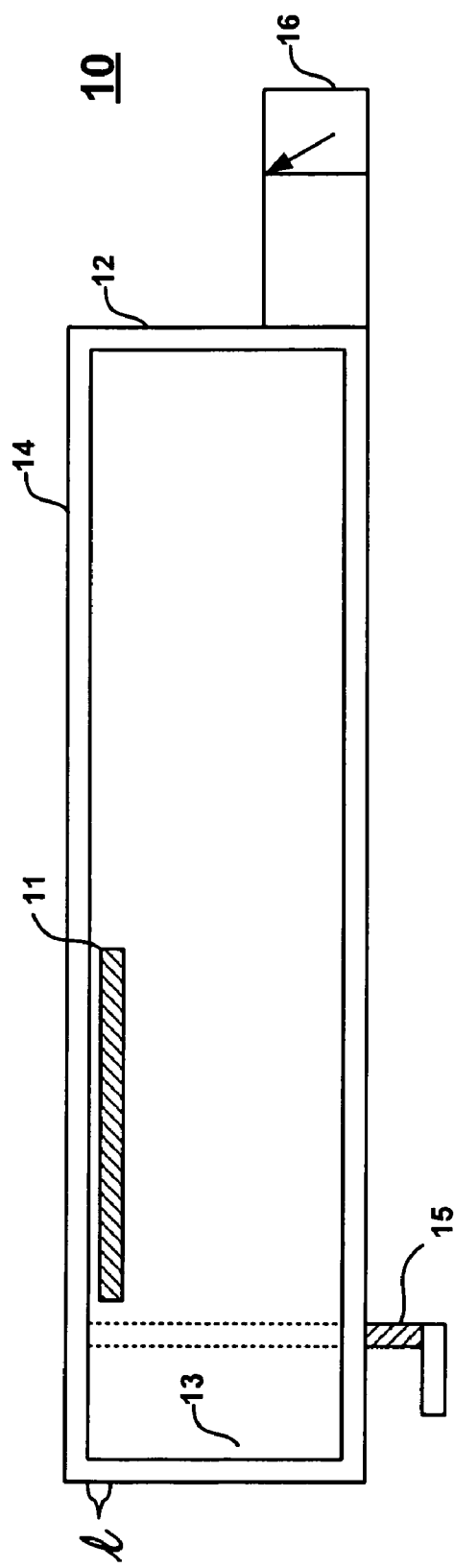
FIG. 4 is a conceptual top view of an acoustic micro-electromechanical viscometer in accordance with the present invention.

Referring now to the drawings, FIG. 4 is a conceptual top view of this invention's acoustic micro-electromechanical viscometer 10, comprising a resonator 11, such as shear wave piezoelectric transducer, submerged in a measurand chamber 12 containing a measurand viscous fluid 13. The piezoelectric transducer 11 is positioned in the measurand chamber 12 at a predetermined separation distance (l) from a rigid, planar, non-resonating boundary 14, which can also function as a side-wall, where the separation distance (l) approximates the penetration depth (δ) of the shear wave in the measurand viscous fluid 13. The chamber 12 also has a sealable lid which is not shown in this drawing. In accordance with the present invention, the separation distance (l) can be adjusted by moving the rigid, planar, non-resonating boundary 14 with a means for lateral movement 15. The lateral movement means 15 is depicted as a simple turn-screw, but it can be any mechanical or hydraulic arrangement that serves to move the non-resonating piezoelectric boundary 14 without disturbing the acoustic motion of the transducer 11. Measurements can be taken with a means for monitoring viscosity 16, which could include a means for data processing or an appropriate meter. Peripheral equipment such as the resonator mounting structure, electrodes, and cables are well-known to those skilled in the art and are not shown in these drawings.

The shear wave piezoelectric resonator 11 produces acoustic motion in the measurand viscous fluid 13 and also senses the effects of the acoustic motion on that fluid 13. In accordance with the present invention, when the resonator 11 is driven at a selected frequency an evanescent shear mode wave is generated in the measurand viscous fluid 13 that causes a mechanical admittance and a mechanical impedance in a thin fluid layer between the resonator 11 and boundary 14 allowing the monitoring means 16 to measure given viscosity independently from the given mass density at an increased level of accuracy.

It should be noted that this invention's measurand chamber 12 is configured to allow adjustment of the predetermined separation distance (l) through lateral movement of the rigid, planar, non-resonating boundary 14 and that these features are essential elements of this invention that are unknown in prior art measurand tanks.

A number of variations of this invention's acoustic micro-electromechanical viscometer 10 are possible, such as the resonator 11 being a piezoelectric resonator, the boundary 14 being another resonator, the other resonator being driven at an identical frequency to the selected frequency with either a phase advancement or retardation. The resonator 11 could also be a piezomagnetic resonator. Other variations include numerous shapes and sizes for the driving mechanism such as a flexural mode cantilever, i.e. diving board shape, containing a pattern of one, a few, or many tiny holes through the thickness, with the holes having apertures with diameters that are comparable to the penetration depth (δ). By executing flexural motion, like a diving board, the fluid 13 would be forced through the openings, back and forth, with each "flap" of the cantilever. The mathematics would be much more difficult than the present instance, but the concept is the same: fluid confined in a space of dimension having the general size of the penetration depth in the fluid. Additionally, a cantilever having holes of varying sizes e.g. a diving board that looks like a narrow slice of Swiss cheese, could be used for various fluids of different viscosities.

FIGS. 5A and 5B are top and end conceptual views of another embodiment of this invention's acoustic micro-electromechanical viscometer 20 where like numerals are employed for like structures. Referring now to the drawings, FIG. 5A depicts a top view of this invention's narrow acoustic micro-electromechanical viscometer 20, comprising a means for generating an acoustic wave 11, such as a shear wave piezoelectric resonator, submerged in a narrow and shallow measurand chamber 22 containing a measurand viscous fluid 13. The acoustic wave generating means 11 is positioned in the narrow measurand chamber 22 at a predetermined separation distance (l) from a rigid, planar, non-resonating boundary 24, where the separation distance (l) approximates the penetration depth ($\delta$) of the shear wave in the measurand viscous fluid 13. In accordance with the present invention, the separation distance (l) can be adjusted by moving the rigid, planar, non-resonating boundary 24 with a means for lateral movement 25. The lateral movement means 25 is depicted as a simple turn-screw, but can be any mechanical or hydraulic arrangement that moves the non-resonating boundary 24 without disturbing the acoustic motion of the acoustic wave generating means 11. A viscosity monitoring means 16 is available for taking acoustic measurements, and could be configured with a data processing means or an appropriate meter. Peripheral equipment such as the resonator mounting structure, electrodes, and cables are not shown in these drawings.

FIG. 5B is a conceptual end view of this invention's narrow acoustic micro-electromechanical viscometer 20, that is enlarged and not drawn to scale, depicting the acoustic wave generating means 11 submerged in the narrow measurand chamber 22 along with the predetermined separation distance (l) of the shear wave in the measurand viscous fluid 13. The lateral movement means 25 can be positioned inside or outside the chamber 22 so long as the acoustic motion of the transducer 11 is not disturbed. It should be noted that this invention's measurand chamber 22 is configured to be more narrow and shallow than the typical prior art measurand tank and that the predetermined separation distance (l) and the rigid, planar, non-resonating boundary 24 are essential elements of this invention that are unknown in prior art measurand tanks. Many of the variations of the first embodiment of the present invention also apply here as well.

In order to display the range and generality of the present invention, Tables I through V are included. These demonstrate that, for a representative sample of fluids, the penetration depth ($\delta$) at frequencies ordinarily employed for viscosity measurements, is generally on the order of micrometers. The sample fluids include both liquids and gases. The present invention is thus inherently sub-miniature, and in line with the generally construed appellation "MEMS", or "micro-electromechanical."

Rayleigh, p. 313 of the *Theory of Sound, Vol. 2*, 2nd revised edition, remarks: "Both by theory and experiment the remarkable conclusion has been established that within wide limits the force [viscosity] is independent of the density of the gas." Tables I and II contain values of pertinent acoustic properties of argon at 200° K, ($\eta$=2.125 $10^{-5}$ Pa-s), and hydrogen at 400° K, ($\eta$=1.0867 $10^{-5}$ Pa-s). In these tables and those below, the $\delta$ values are for a frequency of 1 MHz. The formula for penetration depth ($\delta$) is $\delta = \sqrt{2\eta/\rho\omega}$, and thus $\delta$ varies as the reciprocal of the square root of the frequency; for a frequency of 10 MHz, the tabular entries for $\delta$ would be smaller by a factor of $\sqrt{(10)}$ 3.16.

TABLE I

Acoustic parameters of water/glycerol mixtures

| $H_2O/C_3H_8O_3$ volume % | $\rho$ kg/m³ | $v_L$ m/s | $\eta$ Pa·s | $\delta$ μm |
|---|---|---|---|---|
| 25% water | 1205 | 1738 | 0.046 | 3.486 |
| 20% water | 1217 | 1765 | 0.076 | 4.458 |
| 15% water | 1228 | 1798 | 0.13 | 5.805 |
| 10% water | 1239 | 1828 | 0.25 | 8.014 |
| 05% water | 1250 | 1870 | 0.58 | 12.15 |
| 00% water | 1260 | 1909 | 1.5 | 19.47 |

TABLE II

Acoustic parameters of various fluids

| Substance | T °C. | $\rho$ kg/m³ | $\eta$ mPa-s | $\delta$ μm |
|---|---|---|---|---|
| Water | 0 | 999.8 | 1.79 | 0.755 |
| Water | 20 | 998.2 | 1.00 | 0.565 |
| Water | 100 | 958.4 | 0.28 | 0.305 |
| Vapor | 100 | 0.6 | 0.013 | 2.626 |
| whole blood | 37 | 1060 | 3.5 | 1.023 |
| ethyl alcohol | 20 | 789.20 | 1.15 | 0.680 |
| Helium | 0 | 0.1786 | 18.6 | 5.758 |
| mercury | 15 | 13,550 | 1.55 | 0.191 |
| SAE 10 | 20 | 875 | 65 | 4.863 |
| SAE 20 | 20 | 885 | 125 | 6.705 |
| SAE 30 | 20 | 890 | 200 | 8.458 |
| SAE 40 | 20 | 900 | 319 | 10.622 |
| glycerine | 25 | 1258.02 | 1420 | 18.955 |

TABLE III

Acoustic parameters of Argon

| Pressure Atm | $R_S$ kg/(s·m²) | $\delta$ μm | $R_S$ kg/(s·m²) | $\delta$ μm | $R_S$ kg/(s·m²) | $\delta$ μm |
|---|---|---|---|---|---|---|
| 0.01 | 1.115 | 14.58 | 1.081 | 21.21 | 1.047 | 27.38 |
| 0.1 | 3.526 | 4.609 | 3.420 | 6.708 | 3.311 | 8.659 |
| 1 | 11.16 | 1.456 | 10.82 | 2.121 | 10.47 | 2.738 |
| 10 | 35.79 | 0.4541 | 34.30 | 0.6687 | 33.11 | 0.8658 |
| 100 | 134.0 | 0.1212 | 110.64 | 0.2073 | 104.4 | 0.2746 |
| T → | 200° K | | 300° K | | 400° K | |

$R_S$ is the mechanical resistance at large values of $\delta$.

TABLE IV

Acoustic parameters of hydrogen

| Pressure atm | $R_S$ kg/(s·m²) | $\delta$ μm | $R_S$ kg/(s·m²) | $\delta$ μm | $R_S$ kg/(s·m²) | $\delta$ μm |
|---|---|---|---|---|---|---|
| 0.01 | 0.1620 | 42.02 | 0.1520 | 59.01 | 0.1450 | 75.05 |
| 0.1 | 0.5130 | 13.29 | 0.4800 | 18.66 | 0.4580 | 23.73 |
| 1 | 1.621 | 4.203 | 1.518 | 5.903 | 1.448 | 7.506 |
| 10 | 5.110 | 1.333 | 4.787 | 1.872 | 4.568 | 2.379 |
| 100 | 15.63 | 0.4358 | 14.74 | 0.6077 | 14.14 | 0.7684 |
| T → | 200° K | | 300° K | | 400° K | |

TABLE V

Acoustic parameters of Oxygen

| Pressure atm | $R_S$ kg/(s·m²) | δ μm | $R_S$ kg/(s·m²) | δ μm | $R_S$ kg/(s·m²) | δ μm |
|---|---|---|---|---|---|---|
| 0.01 | 0.9540 | 15.57 | 0.9180 | 22.47 | 0.8850 | 28.89 |
| 0.1 | 3.017 | 4.925 | 2.903 | 7.108 | 2.798 | 9.134 |
| 1 | 9.555 | 1.555 | 9.182 | 2.247 | 8.847 | 2.889 |
| 10 | 30.64 | 0.485 | 29.12 | 0.7087 | 27.98 | 0.9135 |
| 100 | 115.1 | 0.1291 | 93.97 | 0.2196 | 88.13 | 0.2900 |
| T → | 200° K | | 300° K | | 400° K | |

We have considered Newtonian fluids subjected to shear motion, in the limit where the distance to a confining rigid wall is comparable to the penetration depth. It is found that the immittance seen at the face of the shear transducer, (and reflected in the transducer equivalent electrical circuit values), permits direct determination separately of the viscosity and mass density. The smallness of the penetration depth, in most applications, is such that extreme miniaturization is thereby enabled.

Referring back to FIG. 4, the present invention also encompasses a method for measuring acoustic viscosity of a measurand viscous fluid independently from the density of the viscous fluid, comprising the steps of forming a measurand chamber 12; filling the chamber with the measurand viscous fluid 13, the viscous fluid 13 having a given penetration depth, δ, a given viscosity, η, and a given mass density, ρ; configuring the chamber 12 with a rigid, planar non-resonating boundary 14, a means for lateral movement 15 to adjust the boundary, and a sealable lid, not shown in this drawing; positioning a means for generating an acoustic wave 11, having at least one surface inside the chamber 12 parallel to the boundary 14; and calculating a predetermined separation distance, l, between the boundary 14 and the surface of the acoustic wave generating means 11 that is comparable to the given penetration depth. The steps of the method continue with setting the boundary 14 at the predetermined distance between the boundary 14 and the acoustic wave generating means 11; providing a thin layer of the viscous fluid 13 between the surface and the boundary 14; connecting a means for monitoring viscosity 16 to the chamber 12; driving the acoustic wave generating means 11 at a selected frequency to generate an evanescent shear mode wave in the viscous fluid 13; causing a mechanical admittance and a mechanical impedance in the thin layer; and allowing the monitoring means 16 to measure the given viscosity independently from the given mass density at an increased level of accuracy.

It is to be further understood that other features and modifications to the foregoing detailed description are within the contemplation of the present invention, which is not limited by this detailed description. Those skilled in the art will readily appreciate that any number of configurations of the present invention and numerous modifications and combinations of materials, components, arrangements, and dimensions can achieve the results described herein, without departing from the spirit and scope of this invention. Accordingly, the present invention should not be limited by the foregoing description, but only by the appended claims.

What I claim is:

1. An acoustic micro-electromechanical viscometer, comprising:
   a chamber is filled with a measurand viscous fluid;
   said viscous fluid having a given penetration depth, δ, a given viscosity, η, and a given mass density, ρ;
   said chamber having a rigid, planar non-resonating boundary, a means for lateral movement to adjust said boundary, and a sealable lid;
   a resonator, having at least one resonator surface, is positioned inside said chamber at a predetermined separation distance, l, between said boundary and said resonator surface, said resonator surface being parallel to said boundary;
   said predetermined separation distance being comparable to said given penetration depth, defines a thin layer of said viscous fluid between said resonator surface and said boundary;
   a means for monitoring viscosity; and
   said resonator being driven at a selected frequency generates an evanescent shear mode wave in said viscous fluid causing a mechanical admittance and a mechanical impedance in said thin layer allowing said monitoring means to measure said given viscosity independently from said given mass density at an increased level of accuracy.

2. The acoustic micro-electromechanical viscometer, as recited in claim 1, further comprising said resonator is a piezoelectric resonator.

3. The acoustic micro-electromechanical viscometer, as recited in claim 1, further comprising said boundary being another resonator.

4. The acoustic micro-electromechanical viscometer, as recited in claim 3, further comprising said another resonator being driven at an identical frequency to said selected frequency.

5. The acoustic micro-electromechanical viscometer, as recited in claim 4, further comprising said another resonator being driven at said identical frequency with a phase advancement.

6. The acoustic micro-electromechanical viscometer, as recited in claim 1, further comprising said resonator is a piezomagnetic resonator.

7. A narrow acoustic micro-electromechanical viscometer device, comprising:
   to a narrow chamber is filled with a measurand viscous fluid;
   said viscous fluid having a given penetration depth, δ, a given viscosity, η, and a given mass density, ρ;
   said chamber having a rigid, planar non-resonating boundary, a means for lateral movement to adjust said boundary, and a sealable lid;
   a means for generating an acoustic wave, having at least one surface, is positioned inside said narrow chamber at a predetermined separation distance, l, between said boundary and said surface, said surface being parallel to said boundary;
   said predetermined separation distance being comparable to said given penetration depth, defines a thin layer of said viscous fluid between said surface and said boundary;
   a means for monitoring viscosity; and
   said acoustic wave means being driven at a selected frequency generates an evanescent shear mode wave in said viscous fluid causing a mechanical admittance and a mechanical impedance in said thin layer allowing said monitoring means to measure said given viscosity independently from said given mass density at an increased level of accuracy.

8. The narrow acoustic micro-electromechanical viscometer, as recited in claim 7, further comprising said acoustic wave generating means is a resonator.

9. The narrow acoustic micro-electromechanical viscometer, as recited in claim 8, further comprising said resonator is a piezoelectric resonator.

10. The narrow acoustic micro-electromechanical viscometer device, as recited in claim 8, further comprising said boundary being another resonator.

11. The narrow acoustic micro-electromechanical viscometer device, as recited in claim 10, further comprising said another resonator being driven at an identical frequency to said selected frequency.

12. The narrow acoustic micro-electromechanical viscometer device, as recited in claim 11, further comprising said resonator being driven at said identical frequency with a phase advancement.

13. The narrow acoustic micro-electromechanical viscometer device, as recited in claim 8, further comprising said resonator is a piezomagnetic resonator.

14. The narrow acoustic micro-electromechanical viscometer, as recited in claim 7, further comprising said acoustic wave means is a flexural mode cantilever.

15. A method for measuring acoustic viscosity of a measurand viscous fluid independently from the density of the viscous fluid, comprising the steps of:
forming a measurand chamber;
filling said chamber with said viscous fluid, said viscous fluid having a given penetration depth, $\delta$, a given viscosity, $\eta$, and a given mass density, $\rho$;
configuring said chamber with a rigid, planar non-resonating boundary, a means for lateral movement to adjust said boundary, and a sealable lid;
positioning a means for generating an acoustic wave, having at least one surface inside said chamber parallel to said boundary;
calculating a predetermined separation distance, l, between said boundary and said surface that is comparable to said given penetration depth;
setting said boundary at said predetermined distance between said boundary and said acoustic wave generating means;
providing a thin layer of said viscous fluid between said surface and said boundary;
connecting a means for monitoring viscosity to said chamber;
driving said acoustic wave means at a selected frequency to generate an evanescent shear mode wave in said viscous fluid;
causing a mechanical admittance and a mechanical impedance in said thin layer; and
allowing said monitoring means to measure said given viscosity independently from said given mass density at an increased level of accuracy.

16. The method for measuring acoustic viscosity of the measurand viscous fluid independently from the density of the viscous fluid, as recited in claim 15, wherein said acoustic wave means is a resonator.

17. The method for measuring acoustic viscosity of the measurand viscous fluid independently from the density of the viscous fluid, as recited in claim 16, wherein said resonator is a piezoelectric resonator.

18. The method for measuring acoustic viscosity of the measurand viscous fluid independently from the density of the viscous fluid, as recited in claim 16, wherein said boundary is another resonator.

19. The method for measuring acoustic viscosity of the measurand viscous fluid independently from the density of the viscous fluid, as recited in claim 16, wherein said resonator is a piezomagnetic resonator.

20. The method for measuring acoustic viscosity of the measurand viscous fluid independently from the density of the viscous fluid, as recited in claim 15, wherein said acoustic wave means is a flexural mode cantilever.

* * * * *